United States Patent [19]

Linder

[11] Patent Number: 5,788,680
[45] Date of Patent: Aug. 4, 1998

[54] DUAL-LUMEN SUCTION CATHETER WITH MULTIPLE APERTURES IN THE VENT LUMEN

[76] Inventor: Gerald Seymour Linder, 16693 Charmel La., Pacific Palisades, Calif. 90272

[21] Appl. No.: 677,390

[22] Filed: Jul. 9, 1996

[51] Int. Cl.⁶ .................................................. A61M 25/00
[52] U.S. Cl. ...................................... 604/280; 604/264
[58] Field of Search .................................... 604/264, 270, 604/280, 282, 284, 43, 902

[56] References Cited

U.S. PATENT DOCUMENTS

| | | | |
|---|---|---|---|
| 4,735,607 | 4/1988 | Keith, Jr. .................. | 604/54 |
| 4,867,747 | 9/1989 | Yarger ..................... | 604/263 |
| 5,078,701 | 1/1992 | Grassi et al. .............. | 604/264 |
| 5,520,662 | 5/1996 | Moss ....................... | 604/246 |

FOREIGN PATENT DOCUMENTS 1443-881-A  12/1988  U.S.S.R. ................. 604/280

*Primary Examiner*—Wynn Wood Coggins
*Assistant Examiner*—Deborah Blyveis
*Attorney, Agent, or Firm*—Cislo & Thomas LLP

[57] ABSTRACT

A dual-lumen suction catheter is disclosed consisting of a longitudinally extending pliable tube having separate and independent suction and vent lumens. The proximal end of the catheter has a first open end for the suction lumen and a second, separate open end, for the vent lumen. The catheter is provided with an opening at its distal end through which fluids to be withdrawn from the organ of a patient enter the suction lumen. A plurality of spaced-apart apertures situated in the distal portion of the catheter extend from within the vent lumen through the wall of the pliable tube to the outside surface of the catheter, the apertures being longitudinally displaced from each other and from the distal tip of the catheter. The plurality of apertures are independent of and separate from the suction lumen.

4 Claims, 1 Drawing Sheet

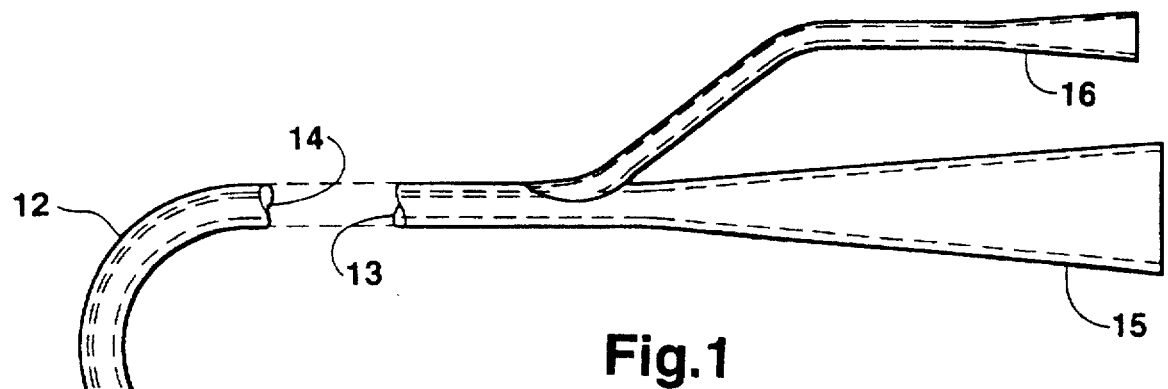
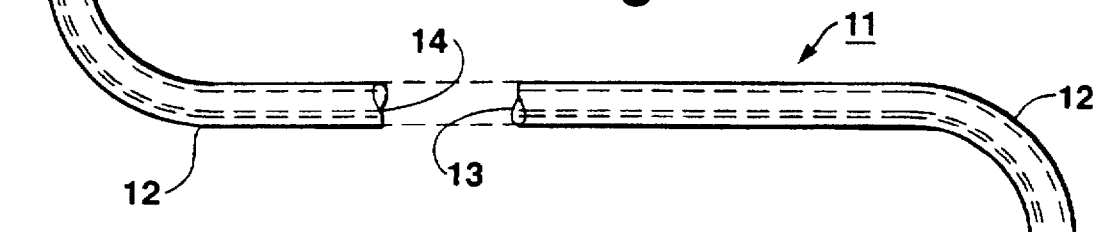
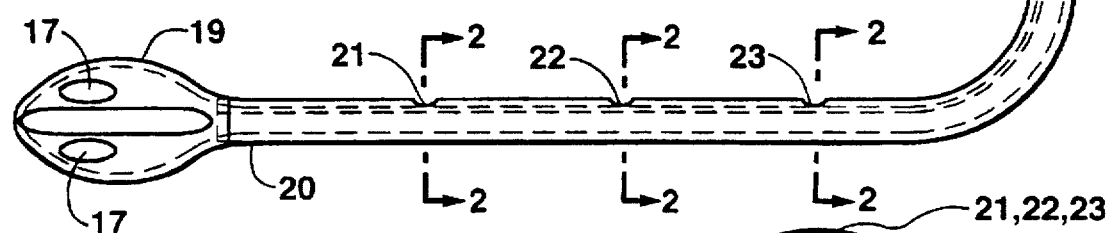
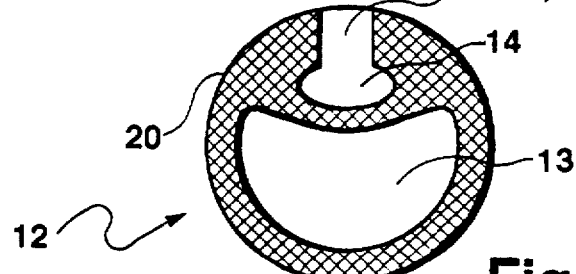
Fig. 1
Fig. 2
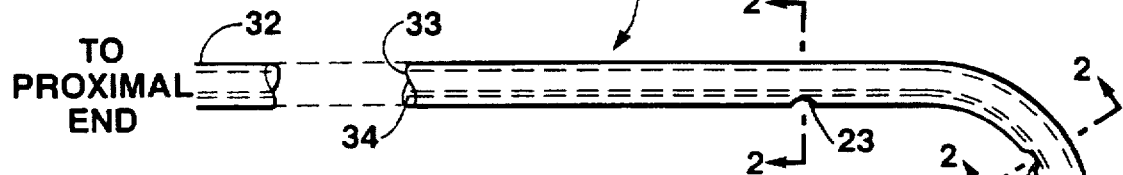
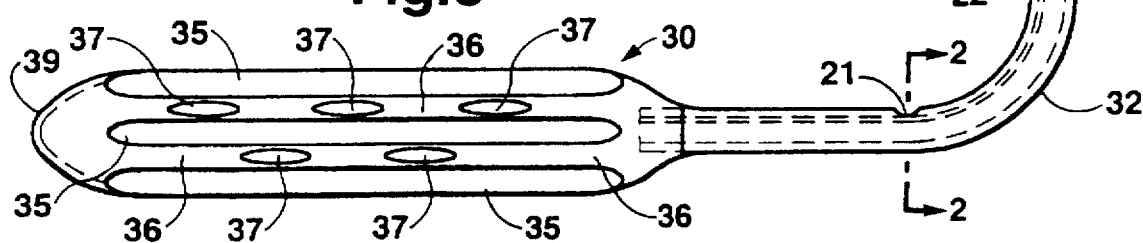
Fig. 3

DUAL-LUMEN SUCTION CATHETER WITH MULTIPLE APERTURES IN THE VENT LUMEN

BACKGROUND OF THE INVENTION

The present invention relates to medical suction catheters and, in particular, to suction catheters of the dual-lumen type. This invention is related, in part, to Applicant's copending application Ser. No. 441,548, filed May 15, 1995, and now U.S. Pat. No. 5,643,232 entitled "Nasogastric Suction Catheter".

The conventional dual-lumen medical suction catheter is specifically designed for the evacuation of the contents of the internal organs of a patient; for example, the urinary bladder, the gall bladder, the stomach and the small intestines. Such catheters are used during emergency surgery in trauma cases, during the time the patient is in intensive cares, in recovery, and, in certain cases, until the patient is released from the hospital.

Since reduced air pressure is present within the suction lumen of the conventional dual-lumen suction catheter, produced by action of the suction pump, it is important that the vent lumen provide air at atmospheric pressure, or above, within the organ of the patient from which the contents are to be evacuated to assure satisfactory operation during the suctioning process.

Due to a number of problems, conventional dual-lumen suction catheters do not always perform in the manner desired. One such problem is the blockage of the suction lumen itself during the suctioning procedures. This occurs when the larger particles within the organ pass through the suction apertures into the suction lumen. If these particles are larger in size and occur in large numbers, the suction lumen becomes blocked and suctioning ceases. It then becomes necessary to flush out the blocked suction lumen, either by air under pressure or by forcing a liquid solution down through the suction lumen from its open proximal end.

Another problem occurs when the vent lumen of the catheter becomes occluded or blocked, thereby preventing air to enter the organ to be evacuated. This blockage effectively arrests the suctioning process. One solution to vent lumen blockage is proposed in U.S. Pat. No. 3,982,540 where an apparatus is disclosed for providing a regulated, small positive air pressure into the open proximal end of the vent lumen. This patent also discloses a modified dual-lumen suction catheter with apertures situated between the vent and suction lumens at the distal end of the catheter to aid in clearing the blockage of suction apertures.

An additional problem, known in the medical arts as gastric reflux, occurs when the contents of the stomach of a patient are forced to enter the vent lumen through a vent aperture or opening by the sudden compression of the walls of the stomach of the patient. This problem occurs when the air pressure within the stomach becomes greater than the normal air pressure within the vent lumen; namely, atmospheric pressure. When gastric reflux occurs, part of the contents of the stomach can be forced up through the vent lumen and out of its open proximal end on to the patient. One simple solution to this problem has been to block the open proximal end of the vent lumen with a plug or cap, although this is frequently overlooked. A proposed solution is suggested in U.S. Pat. No. 4,735,607 wherein a one-way valve is disclosed for insertion into the open prosimal end of the vent lumen, the valve allowing air to enter into the vent lumen but preventing air or fluids from escaping.

BRIEF SUMMARY OF THE INTENTION

The present invention introduces an improved suction catheter of the dual-lumen type to minimize and to alleviate the above-mentioned problems of vent-lumen blockage and gastric reflux by providing the suction catheter with a plurality of vent apertures spaced apart longitudinally from the open distal end of the suction lumen by a distance sufficient to assure that at least one of the vent apertures will be positioned above the level of the contents to be withdrawn from the organ of the patient.

Each of the plurality of vent apertures extends from within the vent lumen out through the wall to the outside surface of the catheter and is separate from and independent of the suction lumen and the suction apertures. Each of the plurality of vent apertures is adapted for the passage of air, at atmospheric pressure or above, from the vent lumen into the organ of the patient whether the vent lumens are above or below the level of the contents of the organ being withdrawn. The vent apertures are spaced apart from each other and may vary in number. As long as one of the plurality of spaced-apart vent apertures remains above the level of the contents of the organ, vent lumen blockage does not occur, and gastric reflux of the contents within the organ into the vent lumen is eliminated.

A primary object of the invention is to provide an improved suction catheter of the dual-lumen type wherein the vent lumen is provided with a plurality of longitudinally spaced-apart vent apertures in the distal end portion of the catheter to assure that adequate air pressure is present within the organ of a patient as the contents of the organ are being withdrawn into the open distal end of the suction lumen of the suction catheter by the suction pump.

Another object of the invention is to provide an improved gastric suction catheter of the dual-lumen type having a plurality of longitudinally spaced-apart apertures into the vent lumen, spaced from the open distal end of the catheter to minimize the possibility of blockage of the vent lumen while the open distal end of the suction catheter is intubated within the stomach of the patient.

Still another object is to provide a dual-lumen nasogastric suction catheter having a plurality of longitudinally spaced-apart apertures into the vent lumen, spaced from the distal end of the catheter to prevent gastric reflux of the contents of the stomach of a patient into the vent lumen while the suction catheter remains positioned within the stomach of the patient.

The above objects of and the brief introduction to the invention will be more fully understood, and further objects and advantages will become apparent, from a study of the following detailed description in connection with the drawings.

BRIEF DESCRIPTION OF THE DRAWINGS

FIG. 1 is a side view of one embodiment of the suction catheter of the invention having three spaced-apart vent apertures into the vent lumen.

FIG. 2 is an enlarged cross-sectional representation of the vent apertures of FIGS. 1 and 3 taken along the lines 2—2.

FIG. 3 is a side view of a nasogastric suction catheter in accordance with the invention with spaced-apart vent apertures into the vent lumen.

DESCRIPTION OF THE INVENTION

The medical suction catheter 11 of the invention illustrated in FIG. 1 consists of a long, slender, hollow, flexible tube 12 having independent first and second lumens 13 and 14 extending the length of tube 12. The first or suction lumen 13 is larger than the second vent lumen 14, and the two lumens are separated one from the other. The vent lumen is identified by the close-spaced parallel broken lines inside the outer surface of flexible tube 12.

The proximal end 15 of suction lumen 13 is enlarged and is open for coupling to the conventional medical suction pump by means of a suction hose. The proximal end 16 of the smaller vent lumen 14 is open to atmospheric pressure or to a separate source of air under a small positive pressure.

The distal end of suction catheter 11 is covered with a short, soft, hollow and ridged bullet-shaped member 19 having a number of recessed suction apertures 17. The contents to be withdrawn from the organ of a patient pass through suction apertures 17 into the open distal end of tube 12 and into suction lumen 13. Suction aperture 17 may be circular or oval in shape and may have a cross-sectional area less than the cross-sectional area of suction lumen 13 to minimize the possibility of blockage of suction lumen 13.

Flexible tube 12 may be made of rubber tubing or medically approved polyvinylchloride tubing. The short, soft, hollow bullet-shaped member 19 may be molded of polyvinylchloride powder and, preferably, is somewhat softer and more resilient than flexible tube 12. Hollow, bullet-shaped member 19 may be made opaque to X-rays by adding a small amount of barium sulfate to the polyvinylchloride powder.

Three vent apertures 21, 22 and 23 extend from within vent lumen 14 out through the wall to the outside surface 20 of flexible tube 12. These vent apertures may be punched or cut into vent lumen 14 from the outside surface 20 of flexible tube 12 by any suitable means and may be circular, oval or slotted in shape. The cross-sectional area of each vent aperture is approximately equal to the cross-sectional area of vent lumen 14.

Vent apertures 21, 22 and 23 are spaced apart from each other and from the suction apertures 17 in hollow, bullet-shaped member 19. The distance between adjacent vent apertures and the distance between vent aperture 21 and suction apertures 17 may vary depending upon the physical size of suction catheter 11 and the size, as well as the age, of the patient. The distance between adjacent vent apertures and between vent aperture 21 and suction apertures 17 is also determined by another factor; namely, the organ of a patient into which the suction catheter is to be intubated. Upon intubation of the organ of a patient to be evacuated, in accordance with the invention, at least one of the vent apertures 21, 22 or 23 should be positioned above the level of the contents to be withdrawn. Since it is not always easy for the physician to know in advance the physical size, exact shape and condition of the organ, a plurality of vent apertures is recommended to assure that at least one is properly positioned. The reasons for this positioning will be discussed hereinbelow.

The cross-sectional representation of vent apertures 21, 22 and 23 is illustrated in FIG. 2. As can be seen, the area of vent lumen 14 is appreciably smaller than the area of suction lumen 13. The cross-sectional area of vent apertures 21, 22 and 23 can be controlled by the length as well as the width and shape of the punch used to form these apertures.

FIG. 3 illustrates a nasogastric suction catheter 31 having a long flexible tube 32 with suction lumen 33 and vent lumen 34. A short, soft, hollow distal end member 30 has its open proximal end bonded to the open distal end of flexible tube 32. Hollow distal end member 30 is similar, in part, to the corresponding hollow distal end member 30 of Applicant's copending application Ser. No. 441,548, filed on May 15, 1995 now U.S. Pat. No. 5,643,230. Hollow distal end member 30 is provided with ridges 35, troughs 36 and a number of suction apertures 37.

The distal end 39 of hollow distal end member 30 is hollow, of bullet shape, and is resiliently collapsible when pressed upon an obstruction. It returns to its original shape upon release of any obstructive force. Hollow distal end member 30 may be made X-ray opaque and may be composed of soft, medically approved polyvinylchloride.

Three vent apertures 21, 22 and 23, the same as illustrated in FIG. 1, extend from within vent lumen 34 out through the wall to the outside surface of flexible tube 32. Vent apertures 21, 22 and 23 are spaced from each other and from suction apertures 37 in the manner and for the same reasons discussed above in connection with suction catheter 11 of FIG. 1.

The physician, when intubating the stomach of a patient with the nasogastric suction catheter 31 of FIG. 3, will be careful to observe the passage of soft, hollow distal end member 31 through the naris, down through the esophagus, past the esophago-gastric sphincter and into the upper part of the stomach. If the air pressure or the gas pressure within the stomach is above atmospheric pressure, the air or gas will enter one of the suction apertures 37 and into suction lumen 33 and pass out of the open proximal end of catheter 31. If the suctioning procedure has commenced, fluids within the upper part of the stomach may enter one or more of the lower suction apertures 37 and into suction lumen 33 and be withdrawn, due in part to the collapsing of the wall of the stomach. As the withdrawal of stomach fluids continues, the using physician may lower soft, hollow distal end member 30 farther into the central portion of the stomach. Once vent aperture 21 has passed the esophago-gastric sphincter at the upper end of the stomachs air at atmospheric pressure is free to pass down vent lumen 34 and pass out through vent aperture 21 into the stomach of the patient. Normal suctioning of the contents of the stomach may continue until air in the stomach begins to enter the upper suction apertures 37 of the catheter. When this condition is observed by the using physician, as by air bubbles in the withdrawn fluids, the soft, hollow distal end member 30 should be lowered even farther into the central area of the stomach, resulting in the passage of vent aperture 22 past the esophago-gastric sphincter and into the upper end of the stomach. Two vent apertures 21 and 22 now are positioned within the stomach. Soft, hollow distal end member 30 may be lowered even farther into the stomach or moved around within the stomach to remove as much of the contents of the stomach as possible before terminating the suction process.

Nasogastric suction catheter 30 of FIG. 3 is frequently left in place within the stomach of the patient upon completion of the suction process and while the patient remains in intensive care or in recovery. If, for any reason, there is a build-up of fluids within the stomach, either by feeding or from bleeding, or from normal gastric fluids, during this period, the possibility of gastric reflux by a sudden compression force upon the fluids by the stomach itself may force the fluids to enter suction apertures 37 and suction lumen 33. While any such fluids may travel the length of the catheter and exit the open proximal end of the suction lumen, they do not enter the vent aperture or apertures as long as at least one vent aperture remains positioned above the level of the fluids within the stomach. The explanation for this feature of Applicant's invention is that the force created within the stomach acting upon the fluids is by an increase in air or gas pressure within the stomach itself, and this increase in air or gas pressure is manifested into the vent lumen by its passage through one or more of the vent apertures 21, 22 or 23. This results in the air within the vent lumen being above that of air at atmospheric pressure and at the same pressure as the compressed air within the stomach above the level of the fluids. Accordingly, stomach fluids are restrained from entry into the vent lumen and must pass, instead, into suction lumen 33 through any of suction apertures 37, the air within the open suction lumen 33 being at atmospheric pressure.

It may be noted that the distal tip of vent lumen 14 of suction catheter 11 of FIG. 1, as well as the distal tip of vent lumen 34 of nasogastric suction catheter 31, may be left open or may be sealed closed, as by means of a cemented plug. Whether the distal tip of the vent lumen is open or is closed, gastric reflux of the fluids within the stomach into the vent lumen is prevented as long as at least one vent aperture remains above the level of the fluids within the stomach.

Since many changes may be made in the above described device and many different embodiments of this invention could be made without departing from the scope thereof, it is intended that all matter contained in the above description or shown in the accompanying drawings shall be interpreted as illustrative and not in a limiting sense.

What is claimed is:

1. A medical suction catheter comprising in combination:
   (a) a long, flexible tube member having independent first and second lumens extending the entire length of said tube member, the first lumen being a suction lumen and the second lumen being a vent lumen;
   (b) said tube member having first and second open proximal ends, the first open end for the suction lumen and the second open end for the vent lumen;
   (c) said tube member having an open distal end for the suction lumen for receiving the contents to be withdrawn from the organ of a patient;
   (d) said first open end of the suction lumen at the distal end of said long, flexible tube member being covered with a soft, resilient and fluid porous member; and
   (e) a plurality of vent apertures situated near the distal end of said tube member, said plurality of vent apertures being spaced-apart longitudinally from each other and from the distal end of said tube member, each of said plurality of spaced-apart vent apertures extending from within said vent lumen out through the wall to the outside surface of said tube member, each of said plurality of spaced-apart vent apertures being adapted for the passage of air from within the vent lumen into the organ of the patient as the contents of the organ are being withdrawn from the organ into the open distal end of said suction lumen of saith catheter.

2. A nasogastric suction catheter comprising in combinations:
   (a) a long, flexible tube member having independent first and second lumens extending the length of said flexible tube member, the first lumen being a suction lumen and the second lumen being a vent lumens;
   (b) said flexible tube member having first and second open proximal ends, the first open end for the suction lumen and the second open end for the vent lumen;
   (c) said flexible tube member having an open distal end;
   (d) a short, soft, hollow distal end member having an open proximal end bonded to the distal end of said flexible tube member, said hollow distal end member having a cylindrical lumen with a diameter approximately equal to the outer diameter of the distal end of said flexible tube member, said hollow distal end member having a plurality of longitudinally extending spaced-apart ridges upon the outer surface thereof, said plurality of spaced-apart ridges being parallel to each other, the space lying between said spaced-apart, parallel ridges and on the outer surface of said soft, hollow distal end member forming troughs between said ridges, said troughs being open at each of their ends;
   (e) a plurality of longitudinally spaced-apart suction apertures located between said parallel ridges and within the troughs of said soft, hollow distal end member, said plurality of suction apertures extending through the bottom of said troughs into the cylindrical lumen of said soft, hollow distal end member; and
   (f) a plurality of vent apertures situated in said flexible tube member, said plurality of vent apertures being spaced apart longitudinally from each other and from the proximal end of said soft, hollow distal end member bonded to the distal end of said flexible tube member, each of said spaced-apart vent apertures extending from within said vent lumen out through the wall to the outside surface of said flexible tube member the distance between adjacent spaced-apart vent apertures being approximately equal to the length of said soft, hollow distal end member.

3. The nasogastric suction catheter as defined by claim 2 wherein the distance between the proximal end of said short, hollow distal end member, bonded to the distal end of said flexible tube, and the nearest longitudinally spaced vent aperture is approximately equal to the length of said short, soft, hollow distal end member.

4. The nasogastric suction catheter as defined by claim 2 wherein said short, soft, hollow distal end member has a hollow, rounded, flexible distal tip, said hollow, rounded, flexible distal tip being resiliently collapsible upon its encounter with any obstruction during intubation of the suction catheter through the naris, esophagus, esophagogastric sphincter, and into the stomach of a patient, said hollow, rounded, flexible distal tip returning to its original shape after passing through any such obstruction.

* * * * *

UNITED STATES PATENT AND TRADEMARK OFFICE
CERTIFICATE OF CORRECTION

PATENT NO. : 5,788,680
DATED : August 4, 1998
INVENTOR(S) : Gerald Seymour Linder It is certified that error appears in the above-indentified patent and that said Letters Patent is hereby corrected as shown below:

Column 1, Line 62, "prosimal" should be proximal.

Column 4, Line 33, "stomachs" should be stomach.

Column 6, Line 2, "lumens" should be lumen.

Signed and Sealed this

Second Day of November, 1999

Attest:

Q. TODD DICKINSON

*Attesting Officer*  Acting Commissioner of Patents and Trademarks